United States Patent [19]

Kessler et al.

[11] 4,082,693

[45] Apr. 4, 1978

[54] CURE MATERIAL FROM LIQUID POLYTHIOPOLYMERCAPTAN POLYMERS FOR DENTAL IMPRESSION TAKING

[75] Inventors: Henry A. Kessler, Succasunna; Phyllis Ying, Morris Plains, both of N.J.

[73] Assignee: Warner-Lambert Company, Morris Plains, N.J.

[21] Appl. No.: 739,410

[22] Filed: Nov. 8, 1976

[51] Int. Cl.² .............................................. B01J 31/26
[52] U.S. Cl. ................................... 252/430; 252/428; 260/79
[58] Field of Search ................................ 252/428, 430

[56] References Cited

U.S. PATENT DOCUMENTS

| 3,192,181 | 6/1965 | Moore | 252/430 X |
| 3,333,021 | 7/1967 | Geipert | 252/428 X |
| 3,850,845 | 11/1974 | Vickery | 252/430 |

*Primary Examiner*—Patrick P. Garvin
*Attorney, Agent, or Firm*—Albert H. Graddis; Frank S. Chow

[57] ABSTRACT

The present invention is concerned with improved dental semi-solid or paste-like elastomeric materials which have the capability of precise surface detail reproduction at ambient and body temperature. Such materials are prepared by treating liquid polysulfide with a synergistic accelerator system comprising a metallic peroxide, e.g., zinc peroxide, 2,2' dithiobisbenzothiazole and 2-mercaptobenzothiazole.

9 Claims, No Drawings

CURE MATERIAL FROM LIQUID POLYTHIOPOLYMERCAPTAN POLYMERS FOR DENTAL IMPRESSION TAKING

The present invention is concerned with compositions of matter ahd, more particularly, the present invention is concerned with improved dental semi-solid or paste-like elastomeric materials which have the capability of precise surface detail reproduction at ambient and body temperature. Still more particularly, the invention is concerned with superior dental impression materials prepared by curing or converting a polysulfide liquid polymer in the presence of a novel accelerator system according to the present invention.

The present invention also includes within its scope the aforesaid accelerator system comprising a metallic peroxide, e.g., zinc peroxide, 2,2' dithiobisbenzothiazole and 2-mercaptobenzothiazole.

As part of the methodology of fitting a dental appliance to patients by methods known in the art, a dental impression material is placed into a dental tray while still in the unset condition. The filled tray is applied to the teeth or mouth structure for a period of time required for the material to set or acquire an elastic set of hardness. The resulting impression is removed and dental stone is poured into the impression and allowed to harden into a permanent cast.

Generally speaking, these dental impression materials are liquid polysulfide polymers. Chemically, the liquid polysulfide polymer such as, for example, Thiokol LP-2 available from Thiokol Chemical Corporation is a polymer of bis(ethylene oxy)methane containing disulfide linkages. The polymer segments are terminated with thiol groups, with side thiol groups occurring "occasionally" in the chain. The average structure of the liquid polysulfide or LP-2 polymer is as follows:

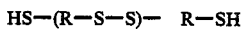

23 wherein R represents an organic group,

The average molecular weight of the Thiokol LP-2 polymer is approximately 4,000.

Lead peroxide is probably the most widely employed curing agent for the polysulfide polymer. One of the disadvantages of this material is in its dark brown unesthetic color which is imparted to the accelerator system and the resultant cure material.

Cumene hydroperoxide represents another type of material used as curing agents in accelerator systems. This organic peroxide is unacceptablle from the standpoint of its irritating odor and bad taste. Organic hydroperoxides, when used in dental products were found to have poor dimensional stability due to the volatility of the hydroperoxide used. Inorganic metallic hydroxides are also employed in accelerator systems. A disadvantage of accelerator pastes containing this material is due to a lack of elasticity of the cured material.

From the aforementioned discussion, it is desirable for an accelerator system to cure the liquid polysulfide polymer into non-irritating, dimensionally stable elastomeric impression material. The cured material should also have superior properties as in regards to body, working qualities, elastic restorability and water insolubility. The material should be free of objectionable odor and taste and be light in color. The material should be non-tacky and have the ability to set rapidly at body temperatures.

It has been found that, in equal volumes, the accelerator system according to the present invention and the polysulfide forms a dental impression material exhibiting substantially all the aforementioned properties.

Broadly speaking, the accelerator system of the present invention comprises about 20% to about 75% by weight of a metallic peroxide, e.g., zinc peroxide, about 5% to about 30% by weight of 2,2' dithiobisbenzothiazole and about 0.05% to about 20% by weight of 2-mercaptobenzothiazole, the remainder being inert fillers alone or in combination with optional additives. The curing potential of the accelerator system is based on the surprising discovery of a synergistic effect of the metallic peroxide and 2,2' dithiobisbenzothiazole. The 2-mercaptobenzothiazole in the system functions to attain the full effect of the zinc peroxide/2,2' dithiobisbenzothiazole.

Prior art suggests that a curing agent having available oxygen is necessary to cure the polysulfide polymer by an oxidative mechanism. The Thiokol LP-2 polymer, for example, is cured by a conversion of the thiol (—SH) groups to disulfide bonds (—S—S—), thus linking the short-chain segments of the polymer to long chains. Although not conclusively demonstrated, the curing reaction, cross-linking or polymerization of polysulfide polymer by the accelerator system of the invention, probably occurs as a result of oxidative and free radical reactions.

In a typical embodiment of the present invention, the polysulfide polymer as well as the accelerator systems are formulated with fillers providing the desired paste-like consistency. Fillers such as zinc oxide, magnesium trisilicate, silicon dioxide, calcium carbonate, titanium dioxide, including flavors and coloring agents, may be incorporated into the final product.

In a preferred embodiment, there are 45 to 55 grams of zinc peroxide, 9.5 to 11.0 grams of 2,2' dithiobisbenzothiazole and 0.5 to 3.0 grams of 2-mercaptobenzothiazole in the accelerator system, per 100 grams of total weight.

In a commercial embodiment, the accelerator system may include optional additives such as fillers, coloring agents, plasticizers and curing promoters or retardants. These additives are known in the art. Please see, for example, U.S. Pat. Nos. 3,046,248 and 3,362,927 and Skinner's *Science of Dental Materials*, 7th Edition (1973).

Examples of fillers which are suitable for the present accelerator system are zinc oxide, calcium carbonate, titanium dioxide and silicon dioxide, alone or in combination. Typically, from 7% to 20% by weight of zinc oxide and 0% to 3% by weight of silicon dioxide are incorporated in the present accelerator system.

Among the retardants there may be mentioned, for example, esters of oleic, stearic and myristic acids such as ethyl oleate. Retardants help to control the working, setting and curing times of the polysulfide polymer. From about 0% to 15% may be included, the final level selected being dependent upon the particular setting time desired. For example, about 7.4% by weight will retard the setting and curing for approximately seven minutes. On the other hand, without the ethyl oleate, in the accelerator system, the polysulfide polymer sets in about three minutes.

Plasticizers which may be included are, for example, 2-ethylhexyl diphenyl phosphate, dibutylphthalate or dioctylphthalate either alone or in combination. Typically, from about 10 to 30% by weight is incorporated in the accelerator system.

The accelerator system of the present invention is prepared by mixing together the ingredients, i.e., 2,2' dithiobisbenzothiazole, 2-mercaptobenzothiazole, selected metallic peroxide, plasticizer, filler, retardant and coloring material by simple blending procedure to obtain a homogenous mixture. The resulting mixture is packaged in a suitable container.

The polysulfide composition is prepared in a manner known per se. Thus, liquid polysulfide such as LP-2 Thiokol liquid polymer is blended with known adjuvant materials such as fillers essential or flavoring oil, and so on, to obtain a homogeneous mixture. The product is packaged into containers by conventional means.

In use, the clinician measures approximately equal volumes of the accelerator system and the liquid polysulfide composition and mixes the two compositions. The resulting composition sets into a non-tacky, rubbery elastomeric product in about 7 minutes at ambient temperature (about 25° Centigrade).

The setting reaction is hastened by elevated temperature and increased humidity. Therefore, the mixture will set more rapidly in the patient's mouth than at ordinary temperature. The working and setting time can be decreased by increasing the proportion of accelerator paste to liquid polysulfide polymer paste. Alternatively, the working and setting time can be increased by increasing the volume of liquid polysulfide polymer paste. Another method of increasing the working and setting time involves decreasing the level of ethyl oleate or other suitable working and setting time retarders (such as other esters of oleic, stearic and myristic acids). By the aforementioned modification in component levels, the formation of the rubber-like elastomer can be readily controlled to set in from 3 to 30 minutes.

In order to further illustrate the practice of the present invention, the following examples are included:

EXAMPLE 1

An accelerator system is prepared by blending together at room temperature the following ingredients:

| 1. | 2,2' Dithiobisbenzothiazole containing 1.33% free 2-mercaptobenzothiazole | 10.29 g. |
|---|---|---|
| 2. | 2-Mercaptobenzothiazole, purified, about* | 0.67 g. |
| 3. | 2-Ethylhexyl diphenyl phosphate | 22.80 g. |
| 4. | Ethyl oleate | 7.42 g. |
| 5. | Colorant | 0.32 g. |
| 6. | Zinc peroxide | 47.72 g. |
| 7. | Silicon dioxide | 0.65 g. |
| 8. | Zinc oxide, a sufficient amount to make | 100.00 g |

*Adjusted, based on the content of 2-mercaptobenzothiazole in Ingredient 1 to give a total content of 2.0%.

The resulting product in the form of a paste is packaged in an aluminum tube.

EXAMPLE 2

A liquid polysulfide polymer paste is prepared by blending the following ingredients:

| 1. | Silicon dioxide colloidal | 0.95 g. |
|---|---|---|
| 2. | LP-2 Thiokol liquid polymer | 75.72 g. |
| 3. | Clove oil | 0.14 g. |
| 4. | Zinc sulfide | 17.04 g. |
| 5. | Magnesium trisilicate | 6.15 g. |

When an equal volume of the composition of Example 1 and an equal volume of this composition are mixed together, a stable elastomeric impression material is formed in about 7 minutes at room temperature.

EXAMPLE 3

The cured material was tested on dogs and was found to be non-irritating.

We claim:

1. An accelerator composition for setting liquid polysulfide polymer for dental impression comprising in combination 5% to 30% by weight of 2,2' dithiobisbenzothiazole, 0.05% to 20% by weight of 2-mercaptobenzothiazole, and 20% to 75% by weight of zinc peroxide, the remainder being inert fillers.

2. The composition of claim 1, containing 2,2' dithiobisbenzothiazole in the amount between 9.5% to 11% by weight, based on the total composition.

3. The composition of claim 1, containing zinc peroxide in the amount between 45% to 55% by weight, based on the total composition.

4. The compositin of claim 1, containing 2-mercaptobenzothiazole in the amount between 0.5% to 3% by weight, based on the total composition.

5. The composition of claim 1, containing dibutylphthalate, dioctylphthalate or 2-ethylhexyl diphenyl phosphate as a plasticizer in the amount between 10% to 30% by weight, based on the total composition.

6. The composition of claim 1, containing ethyl esters of oleic, stearic and myristic acids as a retardant in the amount between 0% to 15% by weight, based on the total composition.

7. The composition of claim 1, containing zinc oxide as the filler in the amount between 7% to 20% by weight, based on the total composition.

8. The composition of claim 1, containing silicon dioxide as the filler in the amount between 0% and 3% by weight, based on the total composition.

9. The composition of claim 6 in which said retardant is ethyl oleate.

* * * * *